（12）United States Patent
Carlucci

(10) Patent No.: US 7,906,478 B2
(45) Date of Patent: Mar. 15, 2011

US007906478B2

(54) PERSONAL-CARE ARTICLES HAVING SELF-ASSEMBLING PEPTIDES

(75) Inventor: Giovanni Carlucci, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 683 days.

(21) Appl. No.: 11/880,353

(22) Filed: Jul. 20, 2007

(65) Prior Publication Data

US 2009/0036851 A1 Feb. 5, 2009

(51) Int. Cl.
*A61K 38/00* (2006.01)
*A61K 51/00* (2006.01)
*A61F 13/02* (2006.01)

(52) U.S. Cl. ......... 514/1.1; 530/326; 530/327; 424/431; 424/1.69

(58) Field of Classification Search ................... None
See application file for complete search history.

(56) References Cited

U.S. PATENT DOCUMENTS

| | | | |
|---|---|---|---|
| 6,350,711 B1 | 2/2002 | Potts et al. | |
| 6,649,099 B2 | 11/2003 | Potts et al. | |
| 6,812,169 B2 | 11/2004 | Potts et al. | |
| 6,867,287 B2 | 3/2005 | Gagliardini et al. | |
| 6,867,344 B2 | 3/2005 | Potts et al. | |
| 6,887,564 B2 | 5/2005 | Gagliardini et al. | |
| 7,635,797 B2 | 12/2009 | Carlucci et al. | |
| 2002/0065495 A1 | 5/2002 | Potts et al. | |
| 2003/0028164 A1 | 2/2003 | Potts et al. | |
| 2003/0124936 A1 | 7/2003 | Potts et al. | |
| 2003/0127767 A1 | 7/2003 | Potts et al. | |
| 2003/0176335 A1* | 9/2003 | Zhang et al. ............. | 514/12 |
| 2005/0287186 A1 | 12/2005 | Ellis-Behnke et al. | |
| 2007/0049888 A1 | 3/2007 | Soerens et al. | |
| 2007/0203062 A1 | 8/2007 | Ellis-Behnke et al. | |
| 2008/0091233 A1* | 4/2008 | Ellis-Behnke et al. ....... | 606/213 |

OTHER PUBLICATIONS

Aguayo, et al., "Growth and Connectivity of Axotomized Retinal Neurons in Adult Rats with Optic Nerves Substituted by PNS Grafts Linking the Eye and the Midbrain" Acad Sci. 495: 1-9, 1987.
Aguayo, et al., "Regrowth and Connectivity of Injured Central Nervous System Axons in Adult Rodents." Acta Neurobiol Exp. 50(4-5): 381-9, 1990.
Aguayo, et al., "Effects of Neurotrophins on the Survival and Regrowth of Injured Retinal Neurons." Ciba Found Symp, 196: 135-44, 1996.
Aleksandrova, et al., "Effect of the Foreign Gene GDNF on Development of Homo-and Xenografts in the Rat Brain." Genetika 36(11): 1553-60, 2000.
Archiblad, et al., "Monkey Median Nerve Repaired by Nerve Graft or Collagen Nerve Guide Tube" J Neurosci 15(5): 4109-4123, 1995.
Arutiunov, et al., "Plastic Repair of Defects in the Dura Mater" Vopr Neirokhir 36(3): 3-8, 1972.
Bernstein, et al., "Effects of Puromycin Treatment on the Regeneration of Hemisected and Transected Rat Spinal Cord" J Neurocytol 7(2): 215-27, 1978.

Bernstein, et al., "Functional and Cellular Responses in a Novel Rodent Model of Anterior Ischemic Optim Neuropathy" Invest Ophthalmol Vis Sci 44(10): 4153-62, 2003.
Bjorklund, et al., "Neural Transplantation for the Treatment of Parkinson's Disease" Lancet Neurol 2(7): 437-44, 2003.
Bromze, et al., "Spinal Axon Regeneration Evoked by Replacing Two Growth Cone Proteins in Adult Neurons." Nat Neurosci 4(1): 38-43, 2001.
Brummelkamp, et al., "A System for Stable Expression of Short Interfering RNAs in Mammalian Cells" Science 296: 550-553, 2002.
Caplan, et al., "Self-Assembly of a Beta-Sheet Protein Governed by Relief of Electrostatic Repulsion Relative to Van Der Waals Attraction." Biomacromolecules 1(4): 627-31, 2000.
Caplan, et al., "Control of Self-Assembling Oligopeptide Matrix Formation Through Systematic Variation of Amino Acid Sequence." Biomaterials 23: 219-227, 2002.
Caplan, et al., "Effects of Systematic Variation of Amino Acid Sequence on the Mechanical Properties of a Self-Assembling, Oligopeptide Biomaterial" J Biomater Sci Polymer Edition 13: 225-236, 2002.
Carter, et al., "Regenerated Retinal Ganglion Cell Axons Form Normal Numbers of Boutons But Fail to Expand Their Arbors in the Superior Colliculus" J Neurocytol 27(3): 187-96, 1998.
Carter, et al., "Regenerated Retinal Ganglion Cell Axons Can Form Well-Differentiated Synapses in the Superior Colliculus of Adult Hamsters." J Neurosci 9(11): 4042-50, 1989.
Chen, et al., "Bcl-2 Promotes Regeneration of Several Axons in Mammalian CNS" Nature 385(6615): 434-9, 1997.
Chen, et al., "Intrinsic Changes in Developing Retinal Neurons Result in Regenerative Failure of Their Axons" Proc Natl Acad Sci USA 92(16): 7287-91, 1995.
Chen, et al., "Long Term Lithium Treatment Suppresses p53 and Bax Expression but Increases Bcl-2 Expression. A Prominent Role in Neuroprotection Against Excitotoxicity." J Biol Chem 274(10): 6039-42, 1999.
Cho, et al., "Ciliar Neurotrophic Factor Promotes the Regrowth Capacity But not the Survival of Intraobitally Axotomized Retinal Ganglion Cells in Adult Hamsters." Neuroscience 94(2): 623-8, 2000.
Cohen, et al., "Neurotrophin-4/5 (NT-4/5) Increases Adult Rat Retinal Ganglion Cell Survival and Neurite Outgrowth in Vitro." J Neurobiol 25(8): 953-9, 1994.
Del Rio, et al., "Proliferation and Differentiation of Glial Fibrillary Acidic Protein-Immunoreactive Glial Cells in Organotypic Slice Cultures of Rat Hippocampus" Neuroscience 43(2-3): 335-47, 1991.
DeVivo, et al., "Epidemiology of Traumatic Spinal Cord Injury" Spinal Cord Medicine 69-81, 2002.
Esser, et al., "CD95(Fas/Apo-1) Antibody-Mediated Apoptosis of Human Retinal Pigment Epithelial Cells" Biochem Biophys Res Commun 213(3): 1026-34, 1995.
Fukuda, et al., "Functional Recovery of Vision in Regenerated Optic Nerve Fibers" Vision Res. 38(10): 1545-53, 1998.
Han, et al., "Development of Biomaterial for Gene Therapy" Mol. Therapy 2: 302-317, 2000.
Heiduschka, et al., "Aurintricarboxylic Acid Promotes Survival and Regeneration of Axomised Retinal Ganglion Cells in Vivo" Nueropharmacology 39(5): 889-902, 2000.

(Continued)

*Primary Examiner* — Maury Audet
(74) *Attorney, Agent, or Firm* — Amanda T. Barry; James E. Oehlenschlager

(57) ABSTRACT

A personal-care article, for receiving body exudates, having a self-assembling peptide is provided.

7 Claims, 3 Drawing Sheets

OTHER PUBLICATIONS

Holmes, et al., "Extensive Neurite Outgrowth and Active Synapse Formation on Self-Assembling Peptide Scaffolds." Proc Natl Acad Sci USA 97(12): 6728-33, 2000.

Huang-Lee, et al., "Effects of Hyaluronan on Collagen Fibrillar Matrix Contraction by Fibroblasts." J Biomed Mater Res 28(1): 123-32, 1994.

Jiang, et al., "Fas Mediates Apoptosis and Oxidant-Induced Cell Death in Cultured hRPE Cells" Invest Ophthalmol Vis Sci 41(3): 645-55, 2000.

Kaplan, et al., "Fas Ligand (CD95 Ligand) Controls Angiogenesis Beneath the Retina" Nat Med 5(3): 292-7, 1999.

Keirstead, et al., "Responses to Light of Retainal Neurons Regenerating Axons into Peripheral Nerve Grafts in the Rat" Brain Res 359(1-2): 402-6, 1985.

Keirstead, et al., "Electrophysiologic Responses in Hamster Superior Colliculus Evoked by Regenerating Retinal Axons" Science 246(4927): 255-7, 1989.

Khodzhaev, et al., "Healing of Meningo-Cerebral Wounds with a Combination of Plastic Repair and Hydrocortisone Therapy Under Clinical and Experimental Conditions." Vopr Neirokhir 4: 35-7, 1976.

Kisiday, et al., "Self-Assembling Peptide Hydrogel Fosters Chondrocyte Extracellular Matrix Production and Cell Division: Implications for Cartilage Tissue Repair" Proc. Natl. Acad. USA 99: 9996-10001, 2002.

Kitchigina, et al., "Functional Integration of the Rat Hippocampal Tissue, Transplanted into the Rabbit Septum." Brain Res 502(1): 39-52, 1989.

Korochkin, et al., "New Approaches in Developmental Genetics and Gene Therapy: Xenotransplantation of Drosophila Embryonic Nerve Cells into the Brain of Vertebrate Animals." Genetika 36(11): 1436-42, 2000.

Kotzbauer, et al., "Neurturin, A Relative of Glial-Cell-Line-Derived Neurotrophic Factor." Nature 384(6608): 467-70, 1996.

Krueger, et al., "Protocol of Thromboembolic Stroke Model in the Rat: Review of the Experimental Procedure and Comparison of Models." Invest Radiol 37(11): 600-8, 2002.

Lambooij, et al., "Apoptosis is Present in the Primate Macula at All Ages." Graefes Arch Clin Exp Ophthalmol 238(6): 508-14, 2000.

Larsson, et al, "Intrastriatal Ventral Mesencephalic Xenografts of Porcine Tissue in Rats: Immune Responses and Fucntional Effects." Cell Transplant 9(2): 261-72, 2000.

Lendahl, et al., "CNS Stem Cells Express a New Class of Intermediate Filament Protein" Cell 60: 585-595, 1990.

Leon, et al., "Mechanical Properties of a Self-Assembling Oligopeptide Matrix." J. Biomater Sci Polym Ed 9(3): 297-312, 1998.

Ling, et al., "Target-Specific Morphology of Retinal Axon Arbors in the Adult Hamster" Vis Neurosci 15(3): 559-79, 1998.

Lundborg, et al., "Nerve Regeneration Model and Trophic Factors in Vivo." Brain Res. 232(1): 157-61, 1982.

Manji, et al., Lithium at 50: Have the Neuroprotective Effects of This Unique Cation Been Overlooked? Biol Psychiatry 46(7): 929-40, 1999.

Manji, et al., "Lithium Up-Regulates the Cytoprotective Protein Bcl-2 in the CNS in Vivo: A Role for Neurotrophic and Neuroprotective Effects in Manic Depressive Illness." J Clin Psychiatry 61(9): 82-96, 2000.

Mansour-Robaey,e t al., "Effects of Ocular Injury and Administration of Brain-Derived Neurotrophic Factor on Survival and Regrowth of Axotomized Retinal Ganglion Cells." Proc Natl Acad Sci USA 91(5): 1632-6, 1994.

Mao, et al., "A Nanomechanical Device Based on the B-Z Transition of DNA." Nature 397(6715): 144-6, 1999.

McCaffrey, et al., "Inhibition of Hepatitis B Virus in Mice by RNA Interference." Nat Biotechnol 21: 639-644, 2003.

McManus, et al., "Gene Silencing in Mammals by Short Interfering RNAs" Nature Rev Gene 3: 737-747, 2002.

Mikkelsen, et al., "Visualization of Efferent Retinal Projections by Immunohistochemical Identification of Cholera Toxin Subunit b" Brain Res Bull 28(4): 619-23, 1992.

Moore, et al., "Lithium Increases N-Acetyle-Aspartate in the Human Brain: In Vivo Evidence in Support of BCL-2's Neurotrophic Effects?" Biol Psychiatry 48(1): 1-8, 2000.

Munter, et al., "Trends in Stroke Prevalence between 1973 and 1991 in the US Population 27 to 74 years of Age" Stroke 33: 1209-1213, 2002.

Nakashima, et al., "Immunological Reaction and Blood-Brain Barrier in Mouse-to-Rat Cross-Species Neural Graft." Brain Res. 475(2): 232-43, 1988.

Paddison, et al., "Short Hairpin RNAs (shRNAs) Induce Sequence-Specific Silencing in Mammalian Cells." Genes Dev 16: 948-958, 2002.

Plant, et al., "Axonal Growth Within Poly (2-Hydroxyethyl Methacrylate) Sponges Infiltrated with Schwann Cells and Implanted into the Lesioned Rat Optic Tract." Brain Res 671(1): 119-30, 1995.

Reinhardt, et al., "Mapping of Nidogen Binding Sites for Collagen Type IV, Heparan Sulfate Proteoglycan and Zinc" J Biol Chem 268(15): 10881-7, 1993.

Remy, et al., "Different Mechanisms Mediate the Rejection of Porcine Neurons and Endothelial Cells Transplanted into the Rat Brain" Xenotransplantation 8(2): 136-48, 2001.

Rende, et al., Immunolocalization of Ciliary Neuronotrophic Factor in Adult Rat Sciatic Nerve. Glia 5(1): 25-32, 1992.

Rosenblat, et al., "Acylated Ascorbate Stimulates Collagen Synethesis in Cultured Human Foreskin Fibroblasts at Lower Doses Than Does Ascorbic Acid" Connect Tissue Res 37(3-4): 303-11, 1998.

Saarma, et al., "Other Neurotrophic Factors: Glial Cell Line-Derived Neurotrophic Factor (GDFN)" Microsc Res Tech 45(4-5): 292-302, 1999.

Sasaki, et al., "Light-dark Discrimination after Sciatic Nerve Transplantation to the Sectioned Optic Nerve in Adult Hamsters." Vision Res 33(7): 877-80, 1993.

Sawai, et al., "Functional and Morphological Restoration of Intracranial Brachial Lesion of the Retinocollicular Pathway by Peripheral Nerve Autografts in Adult Hamsters" Exp Neurol 137(1): 94-104, 1996.

Schmidt, et al., Neural Tissue Engineering: Strategies for Repair and Regeneration Annu. Rev. Biomed. Eng. 5: 293-347, 2003.

Schneider, et al., "Visual Function Due to Regeneration of Optic Nerve or Optic Tract Through Peripheral Nerve Homografts" Soc. Neurosci 26: 611, 2000.

Schneider, et al., "Is it Really Better to Have Your Brain Lesion Early? A Revision of the 'Kennard Principle'" Neuropsychologia 17(6): 557-83-1979.

Snow, et al., "Sulfated Proteoglycans in Astroglial Barriers Inhibit Neurite Outgrowth in Vitro" Exp Neurol 109(1): 111-30, 1990.

Snow, et al., "A Chondroitin Sulfate Proteoglycan May Influence the Direction of Retinal Ganglion Cell Outgrowth." Development 113(4): 1473-85, 1991.

So, et al., "Lesions of Brachium of the Superior Celliculus in Neonate Hamsters: Correlation of Anatomy with Behavior" Exp. Neurol 72(2): 379-400, 1981.

So, et al., "Lengthy Regrowth of Cut Axons from Ganglion Cells After Peripheral Never Transplantation into the Retina of Adult Rats" Brain Res. 382(2): 349-54, 1985.

Stichel, et al., "Inhibition of Collagen IV Deposition Promotes Regeneration of Injured CNS Axons." Eur J Neurosci 11(2): 632-46, 1999.

Stoppini, et al., "A Simple Method for Organotypic Cultures of Nervous Tissue" J Neurosci Methods 37(2): 173-82, 1991.

Suave, et al., "Functional Synaptic Connections Made by Regenerated Retinal Ganglion Cell Axons in the Superior Colliculus of Adult Hamsters" J Neurosci 15(1 Pt2): 665-75, 1995.

Suave, et al., "Topological Specificity in Reinnervation of the Superior Colliculus by Regenerated Retinal Ganglion Cell Axons in Adult Hamsters" J Neurosci 21(3): 951-960, 2001.

Teng, et al., "Functional Recovery Following Traumatic Spinal Cord Injury Mediated by a Unique Polymer Scaffold Seeded with Neural Stem Cells." Proc Natl Acad Sci USA 99(5): 3024-9, 2002.

Thanos, et al., "Type-Specific Stabilization and Target-Dependent Survival of Regenerating Ganglion Cells in the Retina of Adult Rats" J Neurosci. 15(2): 1057-79, 1995.

Thanos, et al., "Regenerating Ganglion Cell Axons in the Adult Rat Establish Retinofugal Topography and Restore Visual Function" Exp. Brain Res. 114(3): 483-491, 1997.

Thomas, et al., "Non-viral Gene Therapy: Polycation-Mediated DNA Delivery. App. Microbiol. Biotechnol." 62: 27-34, 2003.

Varon, et al., "Trophic Mechanisms in the Peripheral Nervous System." Annu Rev Neurosci 1: 327-61, 1978.

Varon, et al., "Trophic Activities for Dorsal Root and Sympathetic Ganglionic Neurons in Media Conditioned by Schwann and other Peripheral Cells." Brain Res 227(1): 73-87, 1981.

Villegas-Perez, et al., "Influences on Peripheral Nerve Grafts on the Survival and Regrowth of Axotomized Retinal Ganglion Cells in Adult Rats." J Neurosci 8(1): 265-80, 1988.

Vogel, et al., "The Role of Glycolipids in Mediating Cell Adhesion: A Flow Chamber Study" Biochim Biophys Acta 1372(2): 205-15, 1998.

Yick, et al., "Peripheral Never Graft and Neurotrophic Factors Enhance Neuronal Survival and Expression of Nitric Oxide Synthase in Clarke's Nucleus after Hemisection of the Spinal Cord in Adult Rat." Exp Neurol 159(1): 131-8, 1999.

Yip, et al., "Axonal Regeneration of Retinal Ganglion Cells, Effect of Trophic Factors" Prog Rein Eye Res 19(5): 559-75, 2000.

Zhang, et al., "Spontaneous Assembly of a Self-Complementary Oligopeptide to Form a Stable Macroscopic Membrane" Proc Natl Acad Sci USA 90(8): 3334-8, 1993.

Zhang, et al., "Self-Complementary Oligopeptide Matrices Support Mammalian Cell Attachment" Biomaterials 16(18): 1385-93, 1995.

Zhang, et al., "Zuotin, a Putative Z-DNA Binding Protein in Saccharomyces Cerevisiae" Embo J 11(10): 3787-96, 1992.

Zhang, et al., "Emerging Biological Materials Through Molecular Self-Assembly." Biotechnology Advances 20: 321-339, 2002.

Zhang, et al., "Biological Surface Engineering: A Simple System for Cell Pattern Formation" Biomaterials 20(13): 1213-20, 1999.

Yang, et al. "Differential Lineage Restriction of Rat Retinal Profenitor Cells in Vitro and in Vivo", Journal of Neuroscience Research 69: 466-476, 2002 Wiley-Liss, Inc.

Sakaguchi, et al. "Transplantation of Neural Progenitor Cells into the Developing Retina of the Brazilian Oppossum: An in vivo System for Studying Stem/Progenitor Cell Plasticity", Developmental Neuroscience, 26: 336-345, 2004 S. Karger AG, Basel.

Buffo, et al. "Targeted Overexpression of the Neurite Growth-Associated Protein B-50/GAP-43 in Cerebellar Purkinje Cells Induces Sprouting after Axotomy But Not Axon Regeneration into Growth-Permissive Transplants", The Journal of Neuroscience, 17(22): 8778-8791, Nov. 15, 1997.

Novikova et al. "Biopolymers and biodegradable smart implants for tissue regeneration after spinal cord injury", Current Opinion in Neurology, 16: 711-715, 2003.

Notice to File Missing Parts of Nonprovisional Application dated Mar. 7, 2005.

Response to Notice to File Missing Parts of Nonprovisional Application dated Sep. 7, 2005.

Amendment Introducing Sequence Listing dated Sep. 7, 2005.

Office Communication, Notice of Non-Compliant Amendment dated Dec. 13, 2005.

Transmittal Letter dated Dec. 21, 2005.

Response to Restriction Requirement dated Jan. 5, 2006.

Office Communication, Office Action Summary dated Oct. 5, 2006.

Office Communication, Office Action Summary dated Mar. 27, 2007.

Office Action Response dated Sep. 27, 2007.

Office Communication, Notice of Non-Compliant Amendment dated Oct. 19, 2007.

Response to Non-Compliant Amendment dated Mar. 13, 2008.

Molecular Self-Assembly of Peptide Nanostructures: Mechanism of Association and Potential Uses, Meital Reches and Ehud Gazit, Current Nanoscience, 2006, 2, pp. 105-111.

Dynamic Reassembly of Peptide RADA16 Nanofiber Scaffold, Hidenori Yokoi, Takatoshi Kinoshita, and Shuguang Zhang, PNAS 2005; 102; 8414-8419; originally published online Jun. 6, 2005; doi: 10.1073/pnas.0407843102, pp. 8414-8419.

Nano Hemostat Solution: Immediate Hemostasis at the Nanoscale, Rutledge G. Ellis-Behnke, PhD, Yu-Xiang Liang, PhD, David K. C. Tay, PhD, hillis W. F. Kau, BSc, Gerald E. Schneider, PhD, Shuguang Zhang, PhD, Wutian Wu, MD, PhD, Kwok-Fai So, PhD, Nanomedicine: Nanotechnology, Biology, and Medicine 2 (2006), Received and Accepted Aug. 22, 2006, pp. 207-215.

Designer Self-Assembling Peptide Nanofiber Scaffolds for 3D Tissue Cell Cultures, Shuguang Zhang, Fabrizio Gelain, Xiaojun Zhao, Seminars in Cancer Bilogy 15 (2005), pp. 413-420.

PCT International Search Report dated Apr. 12, 2010.

* cited by examiner

PERSONAL-CARE ARTICLES HAVING SELF-ASSEMBLING PEPTIDES

REFERENCE TO ELECTRONIC SUBMISSION OF A SEQUENCE LISTING

This application contains a Sequence Listing as an appendix on a compact disc, as required under 37 C.F.R. §1.52(e)(1)(ii) and 37 C.F.R. §1.821(c), which is herein incorporated in its entirety in accordance with 37 C.F.R. §1.77(b)(5). A duplicate disc for the sequence listing is also provided. The compact disc and its duplicate are identical in their contents. The compact disk contains a single ASCI (.txt) file for the sequence listing, the file is entitled "Self-assembling peptides_ST25.txt" and was created on 18 Jul. 2007 using a Windows XP Professional, Version 2002, Service Pack 2 format, and is 8.0 mb in size. All files are Windows XP compatible. A statement that the file and its duplicate on the discs are identical is also submitted separately as required under 37 C.F.R. §1.52(e)(4).

FIELD OF THE INVENTION

The invention relates to personal-care articles, particularly personal-care articles having self-assembling peptides.

BACKGROUND OF THE INVENTION

Personal-care articles are well known for their ability to absorb bodily exudates, for instance menses. Typically, personal-care articles, such as feminine sanitary napkins, include a fluid-permeable topsheet that faces the body of a user, a fluid-impermeable backsheet, and an absorbent core interposed between the topsheet and backsheet. The absorbent core is used to absorb and store the bodily exudates until the personal-care article has been removed.

Absorbent cores are designed not only to absorb an ever greater amount of bodily exudates, but also to store the bodily exudates more securely. The more bodily exudates absorbed by and stored in the personal-care article, the greater the chance that some of the absorbed bodily exudates will exit from the personal-care article (rewet). Various causes can lead to rewet, such as material overload or physical stresses applied to the personal-care article. Whatever the cause, leakage of bodily exudates from a personal-care article is highly undesirable to a user.

The problem of increasing the amount of bodily exudate absorbed and stored by a personal-care article while reducing the occurrence of rewet has not been sufficiently solved by the current personal-care articles. Efforts to increase absorption and prevent rewet have focused on modifying the absorbent core of a personal-care article. Such modifications have involved increasing the amount of absorbent material in the absorbent core or adding materials, such as absorbent gelling materials to the absorbent core. The disadvantage of adding more material to the absorbent layer is that the additional material increases the absorbent core's size and thickness. This adds greater weight to the personal-care article making it more difficult to wear.

It would be desirable to have a personal-care article that absorbs and stores greater amounts of bodily exudate than current personal-care articles. Additionally, it would be desirable to have a personal-care article that could reduce the occurrence of rewet.

SUMMARY OF THE INVENTION

A personal-care article for receiving body exudates is provided that comprises at least one layer including a self-assembling peptide that forms a matrix upon exposure to a bodily exudate.

A tampon is also provided that comprises an absorbent member, wherein the tampon comprises a self-assembling peptide that forms a matrix upon exposure to a bodily exudate.

In addition, a method of storing a bodily exudate in a personal-care article is provided. The method comprises providing a personal-care article comprising a self-assembling peptide, and exposing the personal-care article to a bodily exudate. Upon exposure to the bodily exudate the self-assembling peptide forms a matrix.

DETAILED DESCRIPTION OF THE INVENTION

Figure 1:
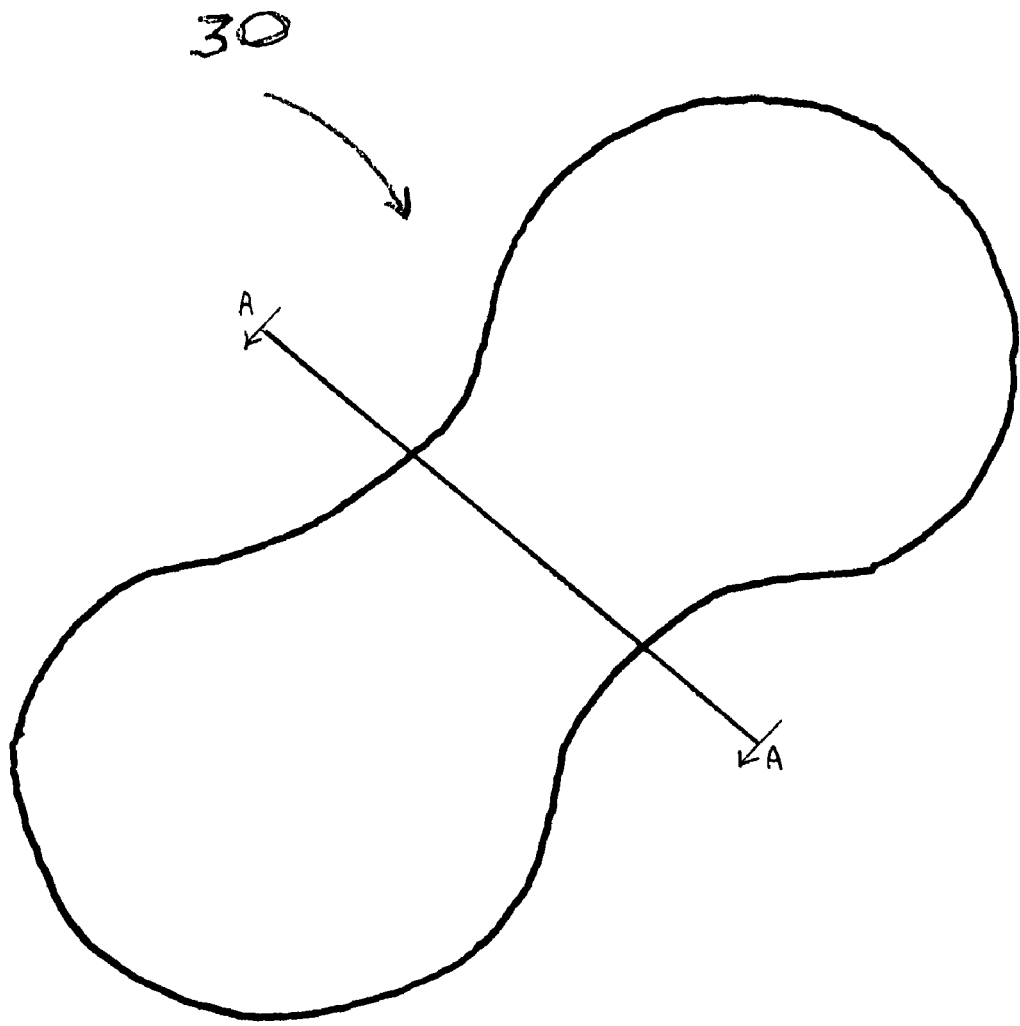
FIG. 1 is a perspective view of a feminine sanitary napkin of the present invention.

The present invention provides a personal-care article, such as a feminine sanitary napkin, having self-assembling peptides. It is believed that the presence of self-assembling peptides in a personal-care article can provide for increased storage capacity of the personal-care article and reduced rewet (the amount of stored bodily exudate, such as menses, that exits the personal-care article during wear). Upon contact with bodily exudates, the self-assembling peptides present in the personal-care article self-assemble into a matrix. The matrix can serve to substantially immobilize the bodily exudates in the personal-care article, such that the bodily exudates cannot readily exit out of the personal-care article or move to other areas of the personal-care article. Therefore, the matrix formed from the self-assembling peptides provides the personal-care article with greater control of absorbed bodily exudates.

As used herein, the term "personal-care article" refers to articles that absorb, block, or contain bodily exudates discharged from the body, and which may be placed within, against or in proximity to the body of a user. Examples of personal-care articles include feminine sanitary napkins, tampons, and interlabial pads, adult incontinence products, training pants, and baby diapers.

As used herein, the term "bodily exudate" is any fluid produced and discharged by a human body or animal body such as menses, urine, vaginal secretions and the like.

As used herein, the term "menses" is a bodily exudate including blood, vaginal secretions and endometrial tissue. The vaginal secretions are mainly composed of mucins. Further, the blood present in menses differs from blood in circulation within the body, in that the blood present in menses does not usually clot, as it is low in fibrinogen. Additionally, in contrast to blood within the body, the blood in menses is often enclosed within or attached to endometrial tissue.

The term "self-assembling peptide" as used herein refers to a peptide formed from a chain of at least two amino acids (α-amino acid residues) linked by covalent bonds, such as peptide bonds, wherein the peptides self-assemble to form matrices upon contact with bodily exudates. Self-assembling peptides may also be branched, in which case they will contain at least two amino acid chains linked by a non-peptide bond. Further, self-assembling peptides can vary in length so long as they can self-assemble. While the amino acid sequences of the self-assembling peptides can vary, in certain embodiments, sequences may include those that provide an amphiphilic nature to the self-assembling peptides, for example the self-assembling peptides can include approximately equal numbers of hydrophobic and hydrophilic amino acids.

The term "self-assemble" as used herein refers to the ability of self-assembling peptides, without requiring the presence of a catalyst or material processing, to form matrices upon exposure to bodily exudates.

The term "matrix" as used herein is a gel structure that is formed when self-assembling peptides are exposed to bodily-fluids. Upon exposure to bodily exudates self-assembling peptides form nanofibers that further form a matrix. While not being limited to theory, it is believed that as the nanofibers form a matrix, bodily exudates are contained within the matrix and substantially immobilized, thus inhibiting further movement of the bodily exudates.

The self-assembling peptides may have, a chain of amino acids conforming to one or more of formulas (A)-(D):

TABLE 1

| | |
|---|---|
| (A) | $((Xaa^{neu} - Xaa^+)_x(Xaa^{neu} - Xaa^-)_y)_n$ |
| (B) | $((Xaa^{neu} - Xaa^-)_x(Xaa^{neu} - Xaa^+)_y)_n$ |
| (C) | $((Xaa^+ - Xaa^{neu})_x(Xaa^- - Xaa^{neu})_y)_n$ |
| (D) | $((Xaa^- - Xaa^{neu})_x(Xaa^+ - Xaa^{neu})_y)_n$ | where: $Xaa^{neu}$ represents an amino acid having a neutral charge at physiological pH; $Xaa^+$ represents an amino acid having a positive charge at physiological pH; $Xaa^-$ represents an amino acid having a negative charge at physiological pH; x and y are integers having a value of 1-4, independently; and n has a value of 1-10.

The self-assembling peptides may have a chain of amino acids where $Xaa^{neu}$ represents alanine, valine, leucine, isoleucine, or glycine; $Xaa^+$ represents arginine, lysine or histidine; and $Xaa^-$ represents aspartic acid or glutamic acid. For example, the self-assembling peptides may have, or may include, the amino acid sequence RADARADARADA (SEQ ID No: 28).

The matrices described herein can be formed through self-assembly of the self-assembling peptides described in U.S. Pat. Nos. 5,670,483; 5,955,343; 6,548,630; and 6,800,481 and in Holmes et al., Proc. Natl. Acad. Sci. USA, 97:6728-6733 (2000); Zhang et al., Proc. Natl. Acad. Sci. USA, 90:3334-3338 (1993); Zhang et al., Biomaterials, 16:1385-1393 (1995); Caplan et al., Biomaterials, 23:219-227 (2002); Leon et al., J. Biomaterials; Sci. Polym. Ed., 9:297-312 (1998); and Caplan et al., Biomacromolecules, 1:627-631 (2000). Examples of self-assembling peptides are shown in Table 2.

TABLE 2

| Name | Sequence (n→c) | Configuration | |
|---|---|---|---|
| RADA16-I | n-RADARADARADARADA-c | I | (SEQ ID NO: 1) |
| RGDA16-I | n-RADARGDARADARGDA-c | I | (SEQ ID NO: 2) |
| RADA8-I | n-RADARADA-c | I | (SEQ ID NO: 3) |
| RAD16-II | n-RARADADARARADADA-c | II | (SEQ ID NO: 4) |
| RAD8-II | n-RARADADA-c | II | (SEQ ID NO: 5) |
| EAKA16-I | n-AEAKAEAKABAKAEAK-c | I | (SEQ ID NO: 6) |
| EAKA8-I | n-AEAKAEAK-c | I | (SEQ ID NO: 7) |
| RAEA16-I | n-RAEARAEARAEARAEA-c | I | (SEQ ID NO: 8) |
| RAEA8-I | n-RAEARAEA-c | I | (SEQ ID NO: 9) |
| KADA16-I | n-KADAKADAKADAKADA-c | I | (SEQ ID NO: 10) |
| KADA8-I | n-KADAKADA-c | I | (SEQ ID NO: 11) |
| EAH16-II | n-AEAEAHAHAEAEAHAH-c | II | (SEQ ID NO: 12) |
| EAH8-II | n-AEAEAHAH-c | II | (SEQ ID NO: 13) |
| EFK16-II | n-FEFEFKFKFEFEFKFK-c | II | (SEQ ID NO: 14) |
| EFK8-II | n-FEFKFEFK-c | I | (SEQ ID NO: 15) |
| ELK16-II | n-LELELKLKLELELKLK-c | II | (SEQ ID NO: 16) |
| ELK8-II | n-LELELKLK-c | II | (SEQ ID NO: 17) |
| EAK16-II | n-AEAEAKAKAEAEAKAK-c | II | (SEQ ID NO: 18) |
| EAK12 | n-AEAEAEAEAKAK-c | IV/II | (SEQ ID NO: 19) |
| EAK8-II | n-AEAEAKAK-c | II | (SEQ ID NO: 20) |
| KAE16-IV | n-KAKAKAKAEAEAEAEA-c | IV | (SEQ ID NO: 21) |
| EAK16-IV | n-AEAEAEAEAKAKAKAK-c | IV | (SEQ ID NO: 22) |
| RAD16-IV | n-RARARARADADADADA-c | IV | (SEQ ID NO: 23) |
| DAR16-IV | n-ADADADADARARARAR-c | IV | (SEQ ID NO: 24) |
| DAR32-IV | n-(ADADADADARARARAR)$_2$-c | IV | (SEQ ID NO: 25) |

TABLE 2-continued

| Name | Sequence (n→c) | Configuration | |
|---|---|---|---|
| EHK16 | n-HEHEHKHKHEHEHKHK-c | N/A | (SEQ ID NO: 26) |
| EHK8 | n-HEHEHKHK-c | N/A | (SEQ ID NO: 27) |
| RADA12-I | n-RADARADARADA-c | I | (SEQ ID NO: 28) |
| RAD12-II | n-RARADADARARA-c | II | (SEQ ID NO: 29) |

"N/A" denotes not applicable.

The list presented in Table 2 is representative rather than exclusive. Other self-assembling peptides can be generated, that differ from those listed in Table 2, for example by replacing a single or multiple amino acids, by inclusion or exclusion of a repeating quartet, or by incorporating one or more cysteine amino acids, as cysteine amino acids may bond with one another through the formation of disulfide bonds that provide increased mechanical strength to the matrices.

To provide for matrix formation, in certain embodiments, the self-assembling peptides are complementary and structurally compatible. For example, to be complementary, the side chains (amino acid R groups) of the self-assembling peptides, which have a β-sheet structure, partition into two faces, a first non-polar face with side chains that have no charge (neutral) at physiological pH, for instance the side chain of an alanine amino acid or other hydrophobic amino acid, and a second polar face with positively or negatively charged ionic side chains at physiological pH. The ionic side chains are complementary to one another in that positively charged and negatively charged amino acids from individual self-assembling peptides can form complementary ionic pairs. For example, a negatively charged side chain from an amino acid in a first self-assembling peptide can ionically bond with a positively charged side chain from an amino acid on a second self-assembling peptide. These self-assembling peptides are therefore called complementary self-assembling peptides and, as shown in Table 2, have at least four different configurations, namely I, II, III, or IV. If the charged amino acids alternate with one positively and one negatively charged amino acid on the polar face (−+−+−+−+), the self-assembling peptides are described as "configuration I;" if the charged amino acids alternate with two positively and two negatively charged residues (−−++−−++) on the polar face, the self-assembling peptides are described as "configuration II;" if the charged amino acids alternate with three positively and three negatively charged residues (+++−−−+++−−−) on the polar face, the self-assembling peptides are describe as "configuration III;" if the charged amino acids alternate with four positively and four negatively charged residues (++++−−−−++++−−−−) on the polar face, they are described as "configuration IV." Configuration I-IV self-assembling peptides are also represented in Table 1 by formulas (A)-(D). Formulas (A)-(D) represent Configuration I self-assembling peptides when x and y are both one, Configuration II self-assembling peptides when x and y are both two, Configuration III self-assembling peptides when x and y are both three, and Configuration IV self-assembling peptides when x and y are both four.

If the charged amino acids in self-assembling peptides are substituted with a like charge, there are no known significant effects on the self-assembly process. For example, positively charged lysines can be replaced by positively charged arginines and negatively charged glutamates can be replaced by negatively charged aspartates. However, if the positively charged residues (lysine and arginine) are replaced by negatively charged residues (aspartate and glutamate), the self-assembling peptides can no longer undergo self-assembly to form matrices, but they can still form a β-sheet structure in the presence of a salt. Other amino acids that form hydrogen bonds, such as asparagine and glutamine, may be incorporated into the self-assembling peptides instead of, or in addition to, charged residues. By changing the alanine residues in the self-assembling peptides to more hydrophobic residues, such as leucine, isoleucine, phenylalanine or tyrosine, the resulting self-assembling peptides have a greater tendency to self-assemble and form self-assembling peptide matrices with enhanced strength. Some self-assembling peptides that have similar amino acids compositions and lengths as the self-assembling peptides described herein form α-helices and random-coils rather than β-sheets that do not form macroscopic matrices. Thus, in addition to complementarity and structural compatibility other factors can, in certain embodiments, determine the formation of macroscopic matrices, such as the self-assembling peptide length, the degree of intermolecular interaction, and the ability to form staggered arrays.

The self-assembling peptides are structurally compatible when they can maintain a sufficiently constant intra self-assembling peptide distance to allow matrix formation. While the intra self-assembling peptide distance can vary, it can be quite small, for example less than about 4 Å (angstroms). However, in certain embodiments the intra self-assembling peptide distance can be larger than this, such as about 10 Å. These distances can be calculated based on molecular modeling such as that disclosed in U.S. Pat. No. 5,670,483, and in certain embodiments may be based on an average of a representative number of distances.

The mixtures of self-assembling peptides as described herein, regardless of the precise form, for example whether in a liquid or powdered form, may include RADA16-I (SEQ ID NO:1) or RADA12-I (SEQ ID NO:28) and EAKA16-I (SEQ ID NO:6) or EAK16-II (SEQ ID NO:18). Other mixtures can include RAD16-II (SEQ ID NO:4), EAKA16-I (SEQ ID NO:6), or EAK16-II (SEQ ID NO:18). In addition, other mixtures can include various lengths of the same self-assembling peptide sequence such as, RADA12-I and RADA16-I or RAD12-II and RAD16-II, or mixtures of configuration I and configuration II self-assembling peptides such as RADA12-I and RADA12-II or RADA16-I and RAD16-II. The use of mixtures of self-assembling peptides rather than a single self-assembling peptide can modulate properties of matrices, such as the speed of assembly and the stiffness of the matrix.

As described above, matrices can be formed of heterogeneous mixtures of self-assembling peptides (mixtures containing more than one type of self-assembling peptide conforming to a given formula, see table 1). However, in certain embodiments, the single type of self-assembling peptides present in a mixture is able to form a matrix by self-assembling. In other embodiments, a heterogeneous mixture of two or more types of self-assembling peptides are used to form a matrix through self-assembling. The self-assembling peptides can be chemically synthesized or purified from natural or recombinantly-produced sources by methods well known in the art. For example, self-assembling peptides can be synthesized using standard fluorenylmethoxycarbonyl (Fmoc) chemistry and purified using high pressure liquid chromatography (HPLC).

The number of amino acids in self-assembling peptides can vary. For example, in certain embodiments, the self-assembling peptides may contain between about 8 amino acids to about 200 amino acids, about 8 to about 36 amino acids, or about 8 to about 16 amino acids. In addition to L-form amino acids the amino acids that form the self-assembling peptides may be amino acid analogs; amino acids of the D-form; and amino acids which have been altered or derivatized by the addition of a chemical group such as an acyl group, a phosphate group, a farnesyl group, an isofarnesyl group, or a fatty acid group. Further, the amino acids of the self-assembling peptides can be naturally occurring or non-naturally occurring amino acids. Non-naturally occurring amino acids have not been found in nature, but can be incorporated into a self-assembling peptide chain, for example D-alloisoleucine (2R,3S)-2-amino-3-methylpentanoic acid and L-cyclopentyl glycine (S)-2-amino-2-cyclopentyl acetic acid. Non-natural amino acids and amino acid derivatives listed in U.S. Pub. No. 2004/0204561 can be used. Naturally-occurring hydrophobic amino acids include Ala, Val, Ile, Met, Phe, Tyr, Trp, Ser, Thr and Gly. The charged amino acids can be basic (positive) amino acids, such as Lys, Arg, His, and Orn; acidic (negative) amino acids, such as Glu and Asp; or amino acids that form hydrogen bonds, such as Asn and Gln.

The carboxyl-terminal residue (c-terminus), amino-terminal residue (n-terminus), or both of a self-assembling peptide may be modified. For example, the carboxyl group of the c-terminus, the amino group of the n-terminus, or both can be modified. The charge at the c-terminus, n-terminus or both can also be modified. For example, a group or radical such as an acyl group (RCO—, where R is an organic group such as, an acetyl group ($CH_3CO$—)) can be present at the n-terminus of a self-assembling peptide to neutralize an "extra" positive charge that may otherwise be present, such as a charge not resulting from the side chain of the n-terminus amino acid. Similarly, a group such as an amine group ($NH_2$) in the form of an amide (CO—$NH_2$) can be used to neutralize an "extra" negative charge that may otherwise be present at the c-terminus, such as a charge not resulting from the side chain of the c-terminus amino acid. The neutralization of charges on a terminus may promote the formation of matrices through self-assembly.

In certain embodiments, prior to self-assembly, the self-assembling peptides may be in the form of a solution by being dissolved or emulsified in a liquid, such as deionized water, that is substantially free of ions such as monovalent ions, or contains a sufficiently low concentration of ions to prevent significant self-assembly of the self-assembling peptides. For example, a liquid with a concentration of ions less than about 5 mM could be used to form a solution. Self-assembly may be initiated or enhanced at any subsequent time by the addition of a bodily exudate, such as menses. A wide variety of ions, including anions and cations whether divalent, monovalent, or trivalent, can be used. For example, matrix formation may be promoted by exposure to monovalent cations such as $Li^+$, $Na^+$, $K^+$, and $Cs^+$, and the concentration of such ions used to induce or enhance self-assembly is typically at least 5 mM. Lower concentrations also facilitate assembly, though at a reduced rate. For example, NaCl at a concentration of between about 5 mM and about 5 M will induce the assembly of matrices within a few minutes. Concentrations of NaCl below 5 mM may also induce matrix assembly, but at a slower rate.

The concentration of self-assembling peptides in a solution or powder formulation can vary. For example, the concentration of self-assembling peptides in a solution can be from about 0.01% w/v (0.1 mg/ml) to about 99% w/v (990 mg/ml), inclusive. In certain embodiments, the concentration of self-assembling peptides prior to forming the matrix can be between about 0.1% (1 mg/ml) and about 10% (100 mg/ml). In some embodiments, the concentration of self-assembling peptides may also be less than about 0.1%. The self-assembling peptides can also be formulated as powders and administered in a powder form. In certain embodiments, powder formulations may have a concentration of self-assembling peptides of about 100%. The concentration of self-assembling peptides can be higher in stock solutions and powdered formulations. The concentration can then be brought to the desired level before use by addition of a diluent, such as deionized water or other powders that do not contain self-assembling peptide.

In certain embodiments, self-assembling peptides can be delivered with a hydrophobic material, such as a pharmaceutically acceptable oil, in a concentration that permits self-assembly, but at a reduced rate. When self-assembling peptides are mixed with a hydrophobic agent such as an oil or lipid the assembly of the self-assembling peptides into a matrix differs from matrix formation in an aqueous environment. The hydrophilic part of the peptide will assemble in such a way to minimize contact with the hydrophobic material, thereby creating a barrier between the two environments. This type of behavior enables the encapsulation of therapeutics or other molecules that can be released from the matrix upon contact with bodily exudates.

Matrix formation through self-assembly may be initiated by components in bodily exudates such as ions, physiological pH of bodily exudates, or the increase in temperature provided by contact with bodily exudates. In one embodiment, the time for self-assembly of a matrix can be 60 seconds or less following contact with bodily exudates, such as menses. In some circumstances, such as where the concentration of self-assembling peptides is low, self-assembly may take longer, for example, up to a minute, 5 minutes, 10 minutes, 30 minutes, an hour, or longer.

When the self-assembling peptides are exposed to bodily exudates the self-assembling peptides form nanofibers that further form three-dimensional porous matrices. In certain embodiments, the nanofibers may be about 10 nm to about 20 nm in diameter, and form pores in a matrix, wherein the pores have a greatest width dimension of about 50 nm to about 100 nm. The matrices can have dimensions large enough to be visible under low magnification, such as about 10-fold or less.

The properties and mechanical strength of the matrices can be controlled through manipulation of the self-assembling peptides contained therein. For example, self-assembling peptides can form matrices having varying degrees of stiffness or elasticity. In certain embodiments, a matrix may be somewhat deformable or compressible after self-assembly, but generally will not substantially flow from one area to another. The matrices typically have a low elastic modulus, for example, in certain embodiments a matrix may have a modulus in the range of from about 1 kPa to about 10 kPa as measured by methods known in the art, such as in a standard cone-plate rheometer. In certain embodiments, a matrix may have a lower elastic modulus (<1 kPa), as the lower value permits structural deformation of the matrix in response to pressure. Stiffness of the matrix can be controlled in a variety of ways, such as by any one or more of the following including changing the length, sequence, or concentration of the self-assembling peptides. Other methods for increasing stiffness can also be employed, such as attaching to a self-assembling peptide, binding molecules that can be subsequently cross-linked or otherwise bonded to one another, such as biotin molecules or amino acids with aromatic rings. The binding molecules can be included at the n- or c-terminus of a self-assembling peptide or attached to one or more amino acids between the termini. The cross-linking of binding molecules may be done in any manner known in the art. For example, biotin may be cross-linked using subsequent addition of avidin, and amino acids having aromatic rings may be cross-linked by exposure to UV light. The extent of cross-linking can be determined by light scattering, gel filtration, or scanning electron microscopy using methods known in the art. Furthermore, cross-linking can be examined by HPLC or mass spectrometry analysis of the matrix after digestion with a protease, such as matrix metalloproteases. Material strength may be determined before and after cross-linking.

Further, the matrices formed can be characterized using various biophysical and optical techniques, such as circular dichroism (CD), dynamic light scattering, Fourier transform infrared (FTIR), atomic force (tension) microscopy (ATM), scanning electron microscopy (SEM), and transmission electron microscopy (TEM). The matrices can also be examined using several standard mechanical testing techniques to measure the extent of swelling, the effect of pH and ion concentration on matrix formation, the level of hydration under various conditions, the tensile strength, as well as the manner in which various characteristics change over the period of time required for the matrices to form and degrade. These methods allow one of ordinary skill in the art to determine which of the various alternatives and self-assembling peptides described herein are most suitable for use in a specific application.

In certain embodiments, self-assembling peptides may be used to absorb and store bodily exudates, such as menses in a personal-care article, for instance a feminine sanitary napkin. Personal-care articles are well known in the art and generally comprise nonwoven materials. Examples of personal-care articles include feminine sanitary napkins, tampons, interlabial pads, adult incontinence products, training pants, and baby diapers. Any layer of a personal-care article may comprise self-assembling peptides. For example, if the personal-care article is a feminine sanitary napkin the self-assembling peptide could be present on or in the topsheet, backsheet, or absorbent core. Further, the self-assembling peptide may be present substantially throughout any layer of a personal-care article, or only in certain areas of a layer. For instance, the self-assembling peptides could be applied only to the area or surface of an absorbent core that will be positioned under the vaginal opening. Further still, the self-assembling peptides can be applied to any surface of a layer, such as the body facing surface of a backsheet.

The self-assembling peptides may be applied to a personal-care article as a dry or lyophilized powder or a liquid wherein the self-assembling peptide is suspended or dissolved in a liquid such as deionized water, or any other form of self-assembling peptide. When in liquid form, the self-assembling peptide may be applied to a personal-care article as a spray, paint, print, injection, or any other method known in the art. In certain embodiments, whether in powder or liquid form, an amount of from about 0.1 grams per square meter ($g/m^2$) to about 500 $g/m^2$ of self-assembling peptide is present on or in the personal-care article. In other embodiments, an amount of from about 1 $g/m^2$ to about 100 $g/m^2$ self-assembling peptide is present on or in the personal-care article. In general, the amount of self-assembling peptide present on or in a personal-care article will vary depending on various factors such as the size of the area to which the self-assembling peptide is applied, or the type of personal-care article. The device used to deliver the material will vary in accordance with the amount.

Figure 2:
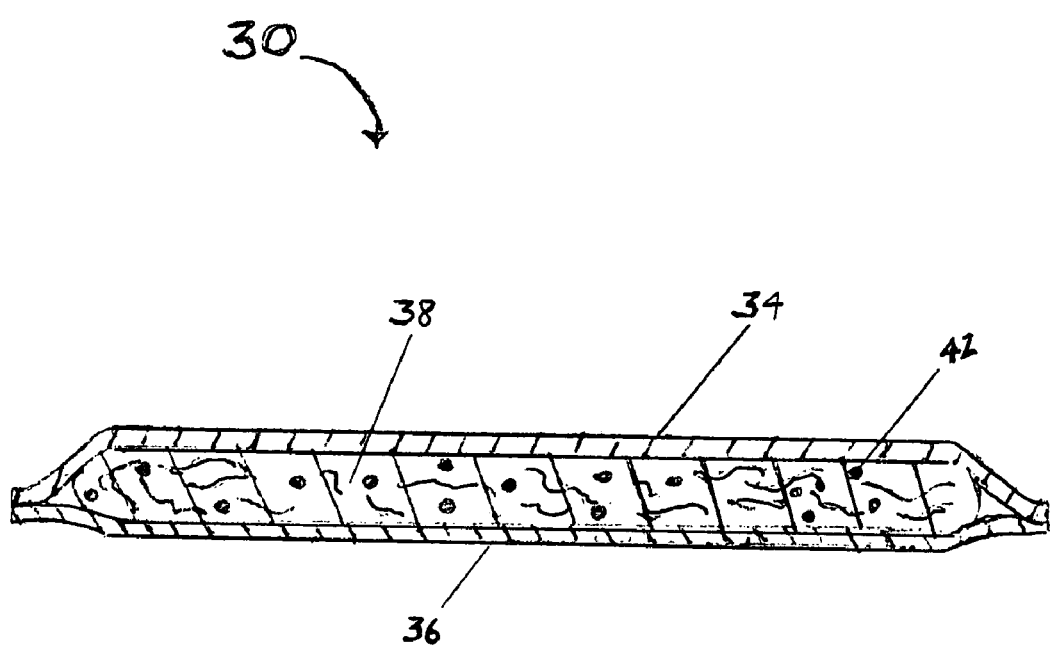
FIG. 2 is a cross-sectional view of section A-A of FIG. 1.

An example of a personal-care article for receiving body exudates, in this instance a feminine sanitary napkin 30, having the self-assembling peptide included in a layer is shown in FIG. 1. A cross-section of a suitable feminine sanitary napkin 30 is shown in FIG. 2 that illustrates the layers of the particular feminine sanitary napkin 30 shown, namely the topsheet 34, backsheet 36, and absorbent core 38.

The topsheet 34 of the feminine sanitary napkin 30 is oriented towards and contacts the body of a wearer to receive bodily discharges. In certain embodiments, the topsheet 34 is liquid pervious, and may be flexible and nonirritating to the skin. Topsheets 34 may be made from nonwoven materials or perforated polyolefinic films or other suitable materials. In certain embodiments, the topsheet 34 may include a plurality of apertures to permit liquids deposited thereon to pass through to the absorbent core 38. Exemplary suitable topsheets 34 may be made in accordance with U.S. Pat. No. 4,342,314 and U.S. Pat. No. 4,463,045.

The backsheet 36 may be any flexible material. In certain embodiments, it may be desirable that the backsheet or a portion thereof is liquid resistant or liquid impervious. The backsheet may, for example include a polyolefinic film, such as a polyethylene film. The backsheet 36 prevents menses absorbed by and stored in the feminine sanitary napkin 30, and particularly menses absorbed by the absorbent core 38, from exiting the feminine sanitary napkin 30 and soiling the clothing and bedding of the wearer. In certain embodiments, the backsheet 36 may also be impervious to malodorous gases generated by absorbed bodily discharges, so that the malodors do not escape and become noticed by the wearer. In certain other embodiments, the backsheet 36 may also permit gases or vapors to pass through it so that it is breathable, while still resisting the passage of liquids therethrough. Further, the backsheet 36 may be made of a soft cloth-like material for example, a polyester or polyolefinic fiber backsheet 36. In certain embodiments, a soft cloth-like backsheet 36 material may be a laminate of a polyester non-woven material lamina, and a film such as described in U.S. Pat. No. 4,476,180.

The absorbent core 38 of the feminine sanitary napkin 30 absorbs and stores menses, particularly menses that traverses through the liquid permeable topsheet 34. In certain embodiments, the absorbent core 38 may store between about four grams to about six grams of menses. Like the topsheet 34 and backsheet 36, the absorbent core 38 may be conformable and nonirritating to the skin. In certain embodiments, the absorbent core 38 may be rectangular or hourglass shaped. In certain embodiments, the absorbent core 38 has two opposed surfaces, one oriented towards the backsheet 36, and one oriented towards the topsheet 34.

The absorbent core 38 may comprise absorbent material. The absorbent material may comprise airfelt, such as cellulose wadding and fibrated communition pulp; tissue paper; absorbent gelling materials; foam; or combinations thereof. Exemplary suitable tissue paper may include tissue paper made in accordance with U.S. Pat. No. 4,191,609 may be used. Exemplary suitable absorbent gelling materials may include absorbent gelling materials made in accordance with U.S. Pat. Re. No. 32,649. Exemplary suitable foam may include foam made in accordance with U.S. Pat. No. 5,260,345 and U.S. Pat. No. 5,387,207.

In certain embodiments, the absorbent core 38 is interposed between the topsheet 34 and backsheet 36. This prevents the absorbent material of the absorbent core 38 from shredding or becoming detached while the feminine sanitary napkin 30 is worn, and to ensure proper containment of menses. The absorbent core 38 may be joined to the topsheet 34 and backsheet 36. Joining may be by bonding the absorbent core 38 to the topsheet 34, or the backsheet 36, using an adhesive. Such adhesive may be applied in a spray pattern, such as a spiral or longitudinally oriented beads.

The self-assembling peptide may be present in at least one of the layers of the feminine sanitary napkin 30, namely the topsheet 34, backsheet 36, or absorbent core 38. For example, as shown in FIG. 2 the self-assembling peptide 42 may be present in the absorbent core 38 of the sanitary napkin 30, as the absorbent core 38 absorbs and stores menses. It is believed, the presence of the self-assembling peptide 42 in the absorbent core 38 of the feminine sanitary napkin 30 provides at least two advantages over prior art feminine sanitary napkins. First, the self-assembling peptides increase the absorbent capacity of the absorbent core by maintaining the absorbed menses in the areas of the absorbent core that initially absorbed the menses. Therefore, the areas of the absorbent core that did not initially absorb the menses remain dry and retain the ability to absorb any additional menses. Second, by immobilizing menses in the absorbent core, the self-assembling peptides, through matrix formation, prevent absorbed menses from exiting out of the absorbent core and contacting the body or undergarments of a user.

Figure 3:
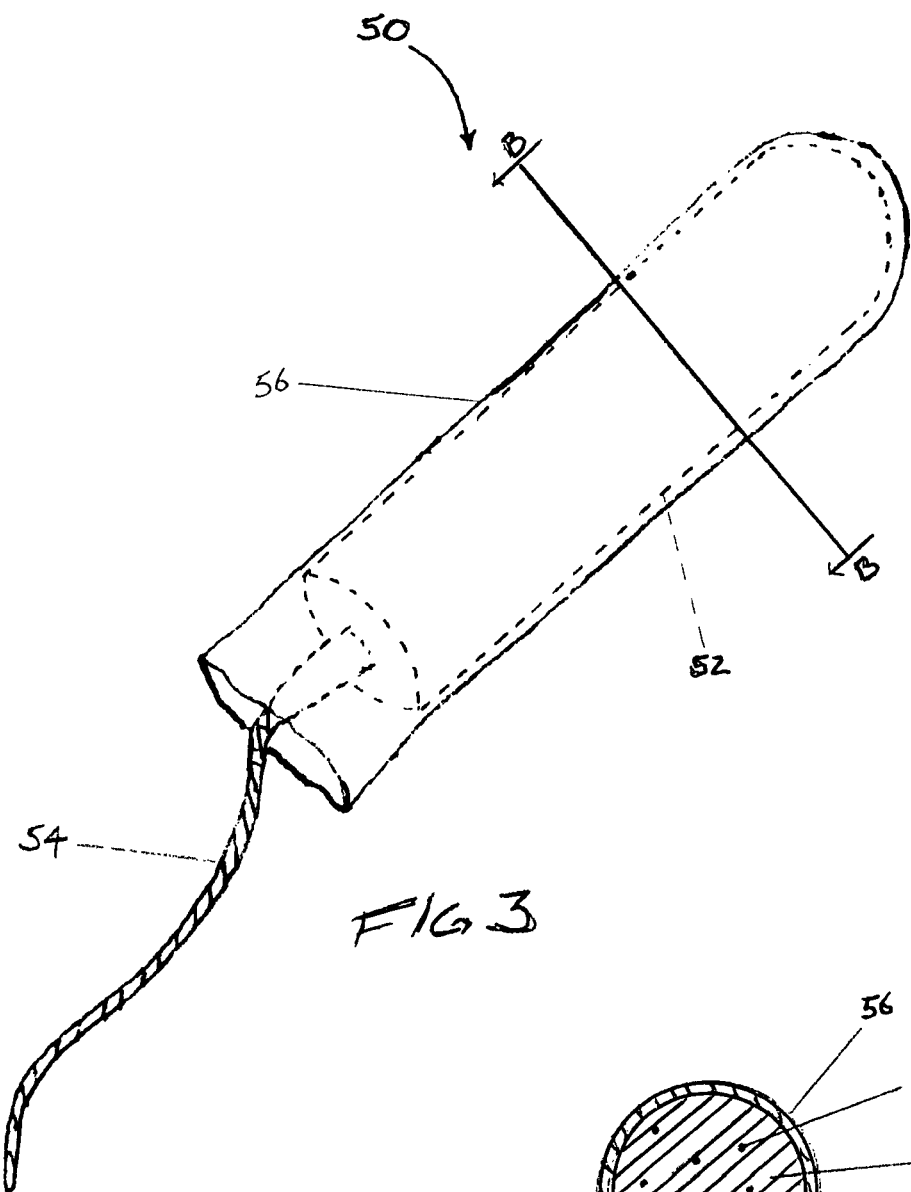
FIG. 3 is a perspective view of a tampon of the present invention.

A further example of a personal-care article, in this instance a tampon 50, having the self-assembling peptide is shown in FIG. 3. The tampon 50 is designed to be inserted into a woman's vaginal cavity to prevent menses from exiting the vaginal opening by contacting and absorbing the flow of menses. The tampon 50 comprises an absorbent member 52, which may be generally cylindrical shaped and a withdrawal means 54. The withdrawal means 54 may be attached to the absorbent member 52, by any manner known in the art, such as sewing, adhesive, thermal bonding, fusion bonding, or combinations thereof.

The absorbent member 52 of the tampon 50 may be constructed from absorbent materials such as fibrous materials. Such fibrous materials may include, but are not limited to synthetic fibers, natural fibers, or combinations thereof. The natural fibers may include, but are not limited to, cotton, wood pulp, flax, hemp, and rayon, such as GALAXY Rayon (a tri-lobed rayon structure) available as 6140 Rayon; or SARILLE L rayon (a round fiber rayon), both available from Kelheim Fibers of Kelheim, Germany, cotton, wood pulp, flax, and hemp. The synthetic fibers can include, but are not limited to, fibers such as polyester, polyolefin, nylon, polypropylene, polyethylene, polyacrylic, vinyl polyacetate, polyacrylate, cellulose acetate, or bicomponent fibers, such as bicomponent polyethylene and polypropylene fibers.

Additional absorbent material include materials such as, peat moss, absorbent foams (such as those disclosed in U.S. Pat. No. 3,994,298), capillary channel fibers (such as those disclosed in U.S. Pat. No. 5,356,405), high capacity fibers (such as those disclosed in U.S. Pat. No. 4,044,766), superabsorbent polymers or absorbent gelling materials (such as those disclosed in U.S. Pat. No. 5,830,543), may be incorporated into the tampon.

In certain embodiments, as shown in FIG. 3, an absorbent member 52 may be substantially covered by an overwrap 56, such as those described in U.S. Pat. No. 6,840,927. The overwrap 56 may be formed from nonwoven fibrous materials or apertured films.

Figure 4:
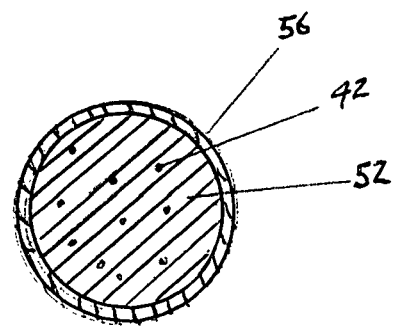
FIG. 4 is a cross-sectional view of section B-B of FIG. 3.

The self-assembling peptide 42 may be present in any layer of the tampon 50, such as the overwrap 56 or absorbent member 52. In certain embodiments, as shown in FIG. 4, which is a cross-sectional view of FIG. 3, the self-assembling peptide 42 may be present in the absorbent member 52 as the absorbent member 52 collects and absorbs menses. It is believed, the presence of the self-assembling peptide 42 in the absorbent member 52 provides the tampon 50 with the advantages over prior art tampons such as increased absorptive capacity as noted previously with reference to the feminine sanitary napkin. In addition, it is further believed the self-assembling peptide reduces the amount of menses lost by a tampon in response to external pressure. As the tampon is in a confined space (the vaginal cavity) the tampon is often subjected to external pressure, especially during removal, which can cause menses to be forced or squeezed out of the tampon. However, as the menses may be immobilized in the matrix formed by the self-assembling peptides the amount of menses lost from the tampon during wear or removal is reduced.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A feminine sanitary napkin for receiving body exudates comprising:
   a topsheet, absorbent core, and backsheet;
   wherein, the absorbent core includes a self-assembling peptide that forms a matrix upon exposure to a bodily exudate, wherein the amino acid sequence of the self-assembling peptide comprises at least one of SEQ ID NO: 1 or SEQ ID NO: 28, wherein the self-assembling peptide is in the form of at least one of a powder or solution.

2. The personal-care article of claim 1, wherein the self-assembling peptide is a powder.

3. The personal-care article of claim 1, wherein the self-assembling peptide is in a solution.

4. The personal-care article of claim 1, wherein the self-assembling peptide is present in the personal-care article in an amount of from about 0.1 g/m$^2$ to about 500 g/m$^2$.

5. The personal-care article of claim 1, wherein the self-assembling peptide is present in the personal-care article in an amount of from about 1 g/m$^2$ to about 100 g/m$^2$.

6. The personal-care article of claim 1, wherein the bodily exudate is menses.

7. The personal-care article of claim 1, wherein the self-assembling peptide is complementary and structurally compatible.

* * * * *

SEQUENCE LISTING

<160> NUMBER OF SEQ ID NOS: 29

<210> SEQ ID NO 1
<211> LENGTH: 16
<212> TYPE: PRT
<213> ORGANISM: Artificial Sequence

```
<220> FEATURE:
<223> OTHER INFORMATION: Self-Assembling Peptides

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 2

Arg Ala Asp Ala Arg Gly Asp Ala Arg Ala Asp Ala Arg Gly Asp Ala
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Self-Assembling Peptide

<400> SEQUENCE: 3

Arg Ala Asp Ala Arg Ala Asp Ala
1               5

<210> SEQ ID NO 4
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 4

Arg Ala Arg Ala Asp Ala Asp Ala Arg Ala Arg Ala Asp Ala Asp Ala
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Self-Assembling Peptide

<400> SEQUENCE: 5

Arg Ala Arg Ala Asp Ala Asp Ala
1               5

<210> SEQ ID NO 6
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 6

Ala Glu Ala Lys Ala Glu Ala Lys Ala Glu Ala Lys Ala Glu Ala Lys
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Self-Assembling Peptide
```

```
<400> SEQUENCE: 7

Ala Glu Ala Lys Ala Glu Ala Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 8

Arg Ala Glu Ala Arg Ala Glu Ala Arg Ala Glu Ala Arg Ala Glu Ala
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Self-Assembling Peptide

<400> SEQUENCE: 9

Arg Ala Glu Ala Arg Ala Glu Ala
1               5

<210> SEQ ID NO 10
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 10

Lys Ala Asp Ala Lys Ala Asp Ala Lys Ala Asp Ala Lys Ala Asp Ala
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: Self-Assembling Peptide

<400> SEQUENCE: 11

Lys Ala Asp Ala Lys Ala Asp Ala
1               5

<210> SEQ ID NO 12
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 12

Ala Glu Ala Glu Ala His Ala His Ala Glu Ala Glu Ala His Ala His
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: Self-Assembling Peptide

<400> SEQUENCE: 13
```

Ala Glu Ala Glu Ala His Ala His
1               5

<210> SEQ ID NO 14
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 14

Phe Glu Phe Glu Phe Lys Phe Lys Phe Glu Phe Glu Phe Lys Phe Lys
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: Self-Assembling Peptide

<400> SEQUENCE: 15

Phe Glu Phe Lys Phe Glu Phe Lys
1               5

<210> SEQ ID NO 16
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 16

Leu Glu Leu Glu Leu Lys Leu Lys Leu Glu Leu Glu Leu Lys Leu Lys
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Self-Assembling Peptide

<400> SEQUENCE: 17

Leu Glu Leu Glu Leu Lys Leu Lys
1               5

<210> SEQ ID NO 18
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 18

Ala Glu Ala Glu Ala Lys Ala Lys Ala Glu Ala Glu Ala Lys Ala Lys
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: Self-Assembling Peptide

<400> SEQUENCE: 19

Ala Glu Ala Glu Ala Glu Ala Glu Ala Lys Ala Lys

```
<210> SEQ ID NO 20
<211> LENGTH: 8
<212> TYPE: PRT
<213> ORGANISM: Artificial Sequence
<220> FEATURE:
<223> OTHER INFORMATION: Self-Assembling Peptide

<400> SEQUENCE: 20

Ala Glu Ala Glu Ala Lys Ala Lys
1               5

<210> SEQ ID NO 21
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 21

Lys Ala Lys Ala Lys Ala Lys Ala Glu Ala Glu Ala Glu Ala Glu Ala
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 22

Ala Glu Ala Glu Ala Glu Ala Glu Ala Lys Ala Lys Ala Lys Ala Lys
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 23

Arg Ala Arg Ala Arg Ala Arg Ala Asp Ala Asp Ala Asp Ala Asp Ala
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 24

Ala Asp Ala Asp Ala Asp Ala Asp Ala Arg Ala Arg Ala Arg Ala Arg
1               5                   10                  15

<210> SEQ ID NO 25
<211> LENGTH: 32
<212> TYPE: PRT
<213> ORGANISM: Artificial Sequence
<220> FEATURE:
<223> OTHER INFORMATION: Self-Assembling Peptide

<400> SEQUENCE: 25

Ala Asp Ala Asp Ala Asp Ala Asp Ala Arg Ala Arg Ala Arg Ala Arg
1               5                   10                  15
```

-continued

```
Ala Asp Ala Asp Ala Asp Ala Asp Ala Arg Ala Arg Ala Arg Ala Arg
                20                  25                  30

<210> SEQ ID NO 26
<211> LENGTH: 16
<212> TYPE: PRT
<213> ORGANISM: Artificial Sequence
<220> FEATURE:
<223> OTHER INFORMATION: Self-Assembling Peptide

<400> SEQUENCE: 26

His Glu His Glu His Lys His Lys His Glu His Glu His Lys His Lys
1               5                   10                  15

<210> SEQ ID NO 27
<211> LENGTH: 8
<212> TYPE: PRT
<213> ORGANISM: Artificial Sequence
<220> FEATURE:
<223> OTHER INFORMATION: Self-Assembling Peptide

<400> SEQUENCE: 27

His Glu His Glu His Lys His Lys
1               5

<210> SEQ ID NO 28
<211> LENGTH: 12
<212> TYPE: PRT
<213> ORGANISM: Artificial Sequence
<220> FEATURE:
<223> OTHER INFORMATION: Self-Assembling Peptide

<400> SEQUENCE: 28

Arg Ala Asp Ala Arg Ala Asp Ala Arg Ala Asp Ala
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Self-Assembling Peptide

<400> SEQUENCE: 29

Arg Ala Arg Ala Asp Ala Asp Ala Arg Ala Arg Ala
1               5                   10
```